(12) United States Patent
Foster et al.

(10) Patent No.: US 9,402,966 B2
(45) Date of Patent: Aug. 2, 2016

(54) APPARATUS AND METHOD FOR PROVIDING IV ACCESS TO THE EXTERNAL JUGULAR VEIN

(71) Applicants: Michael Foster, Boston, MA (US);
Timothy Peck, Boston, MA (US)

(72) Inventors: Michael Foster, Boston, MA (US);
Timothy Peck, Boston, MA (US)

( * ) Notice: Subject to any disclaimer, the term of this patent is extended or adjusted under 35 U.S.C. 154(b) by 204 days.

(21) Appl. No.: 14/203,736

(22) Filed: Mar. 11, 2014

(65) Prior Publication Data
US 2014/0276600 A1    Sep. 18, 2014

Related U.S. Application Data

(63) Continuation of application No. 29/468,781, filed on Oct. 3, 2013, now Pat. No. Des. 725,775, and a continuation of application No. 29/448,541, filed on Mar. 13, 2013, now Pat. No. Des. 720,852.

(60) Provisional application No. 61/886,171, filed on Oct. 3, 2013, provisional application No. 61/779,420, filed on Mar. 13, 2013.

(51) Int. Cl.
*A61M 5/00* (2006.01)
*A61M 5/42* (2006.01)

(52) U.S. Cl.
CPC ........... *A61M 5/425* (2013.01); *A61M 2210/12* (2013.01)

(58) Field of Classification Search
CPC ...................................... A61M 5/425
See application file for complete search history.

(56) References Cited

U.S. PATENT DOCUMENTS

| | | | | | |
|---|---|---|---|---|---|
| 3,463,157 | A | * | 8/1969 | Hunt | A61D 1/00 128/97.1 |
| 4,223,673 | A | * | 9/1980 | Harris | A61M 5/425 294/31.2 |
| 4,619,249 | A | * | 10/1986 | Landry | A61B 5/0059 362/199 |
| D340,113 | S | * | 10/1993 | Knoblauch | D24/143 |
| 5,254,095 | A | * | 10/1993 | Harvey | A61M 5/425 24/563 |
| 5,415,647 | A | * | 5/1995 | Pisarik | A61M 5/425 604/115 |
| D694,401 | S | * | 11/2013 | Lehanneur | D24/113 |
| D694,878 | S | * | 12/2013 | Lehanneur | D24/113 |
| D707,811 | S | * | 6/2014 | Lehanneur | D24/113 |
| 2008/0269677 | A1 | * | 10/2008 | Cull | A61M 1/3653 604/116 |

* cited by examiner

*Primary Examiner* — Emily Schmidt
(74) *Attorney, Agent, or Firm* — ISUS Intellectual Property PLL

(57) ABSTRACT

A device for locating and distending the external jugular vein is provided by a wish-bone shaped apparatus designed to engage the neck of a patent and apply sufficient pressure on the neck that the external jugular vein becomes distended due to pressure placed on the patient's neck. The device includes two distally placed flat portions that resiliently engage the patient's neck without causing choking or hindrance in breathing.

7 Claims, 8 Drawing Sheets

US 9,402,966 B2

APPARATUS AND METHOD FOR PROVIDING IV ACCESS TO THE EXTERNAL JUGULAR VEIN

RELATED APPLICATIONS

This application claims priority to U.S. Provisional Application No. 61/886171, filed Oct. 3, 2013, as well as U.S. Design Pat. No. 29/468,781, filed Oct. 3, 2013, the entire disclosures of which applications are incorporated by reference herein. This application also claims priority to U.S. Provisional Application No. 61/779,420, filed Mar. 13, 2013 as well as U.S. Design Pat. No. 29/448,541, filed Mar. 13, 2013, the entire disclosures of which applications are incorporated by reference herein.

FIELD OF THE INVENTION

This invention relates to medical instrumentation and in particular in improvements in medical instrumentation and techniques to allow physicians and other medical personnel access to a patient's external jugular vein.

BACKGROUND

It is a common medical procedure for medical practitioners to need to have access to the external jugular vein located on either side of a person's neck to allow access for an IV catheter or other cannula to allow for the flow of medicines and other liquids into the patient's bloodstream.

In patients with difficult peripheral venous access, the external jugular vein is a common secondary site for attempted intravenous cannulation. Unlike other superficial veins, due to the anatomy of the neck, there is no available tourniquet to occlude the external jugular vein without disrupting breathing or blood flow.

At the present time and depending, at least in part, on the physiology of a particular patient, the external jugular vein may or may not be prominent and the insertion of an IV may be difficult to perform in normal circumstances. The inability to be able to isolate the external jugular vein (EJ) may result in the delay in medical treatments and even death if the physician is not able to obtain access.

One of the present procedures which is utilized in the medical profession to enlarge the EJ is the Trendelenburg procedure. This procedure involves elevating the patient on the operating or other table to a position in which the head is down and the feet of the patient lie higher than the head. This inclination tends to induce a blood flow into the head and thus, hopefully, make the EJ more visible so that an IV may be introduced. The problem with this procedure is that one has to be concerned, particularly with overweight patients, that the patient will slip off the now inclined operating table. It also has a disadvantage that the procedure must be set up and the patient secured on the operating table and then the operating table inclined, thus causing a unnecessary extension of the time in which a procedure will be required to be performed. It also makes the patient uncomfortable in that the patient's head is in a down position and blood rushes towards the head.

Therefore, there is a need for a simple, cheap, solution that provides the results of the Trendelemburg procedure yet does so without discomfort or danger to the patient, and is done with an apparatus that is cheap, simple and disposable in a procedure which is straightforward.

SUMMARY OF THE PRESENT INVENTION

In one aspect, a device for engaging the external jugular vein of a living body comprises a wishbone shaped frame, the frame having a closed end and an open end.

The open end has two legs, each leg being connected to the closed end and each having an end surface located distally of the closed end, and each end surface is constructed and arranged to face the other end surface on the opposite leg. The end surfaces are separated by a distance less than the thickness of the neck of the living body. When the device is placed in contact with the living body, one or more of the end surfaces engages and causes a distention of at least one external jugular vein.

In another aspect, the device is constructed from a substantially resilient material to allow the one or more end surfaces to press against one or more jugular veins. The closed end and the open ends are non-coplanar and are angularly offset and the angular offset ranges from about 12 degrees to about 50 degrees.

In yet another aspect, the end surfaces comprise generally flat surfaces, and the generally flat surfaces face each other. Each flat surface has an end portion and the distance between the end portions most distal from the closed end is greater than the distance between the end portion less distal from the closed end. The distances may range from about 50 mm to about 82.5 mm.

In a further aspect, a handle is operatively associated with the closed end.

In another aspect, a method of providing access to the external jugular vein of a living human patient includes providing a device constructed as discussed above; then approaching the neck of the patient with the device through the open end of the device; then engaging the neck of the patient with the device until the external jugular vein becomes distended. By this method the external jugular vein thus distended is accessed.

BRIEF DESCRIPTION OF THE DRAWINGS

Preferred embodiments of the present invention are set forth in the following brief description of the drawings and a detailed description illustrating that which is shown in the drawings.

DETAILED DESCRIPTION

Figure 1:
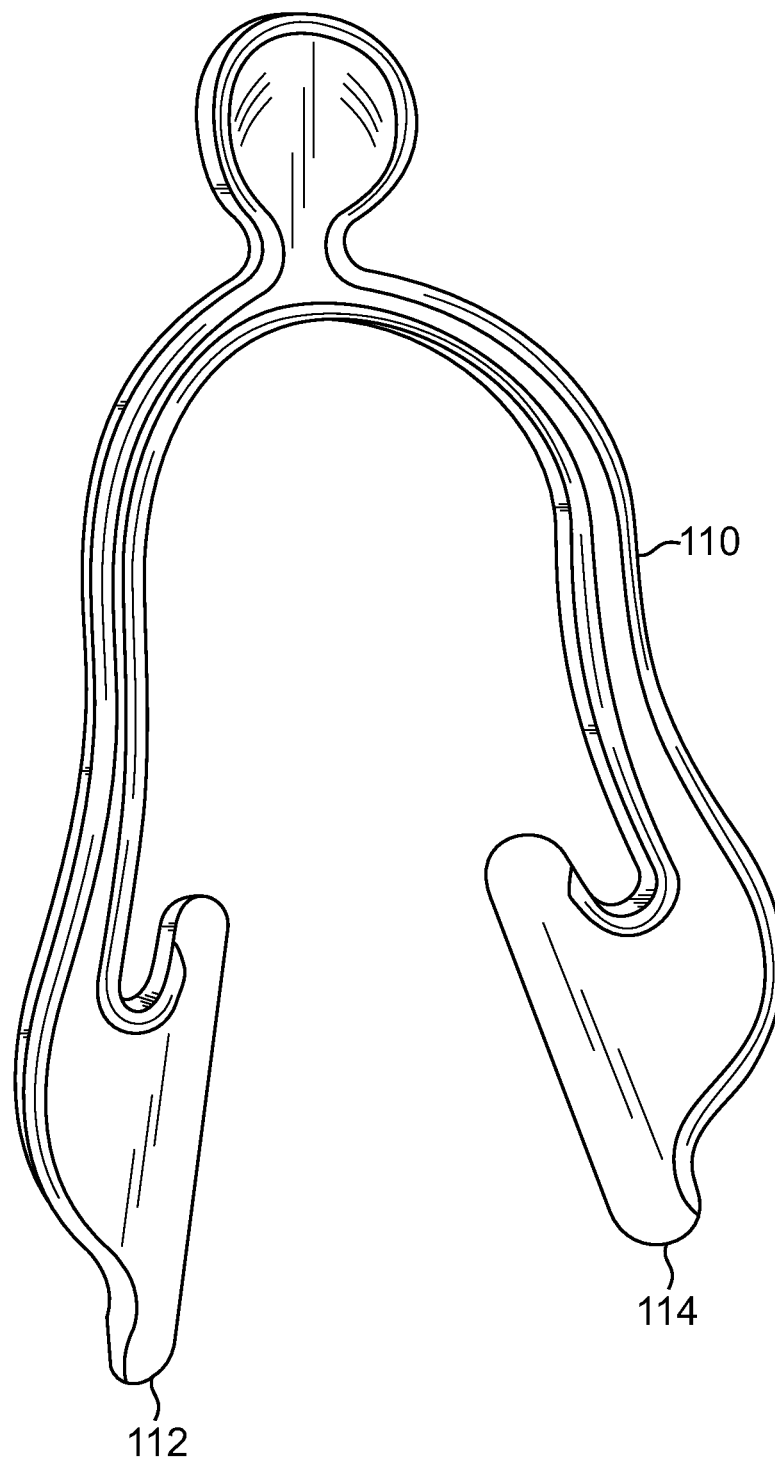
FIG. 1 is a front perspective view of the device of the present invention taken from one perspective.
Figure 7:
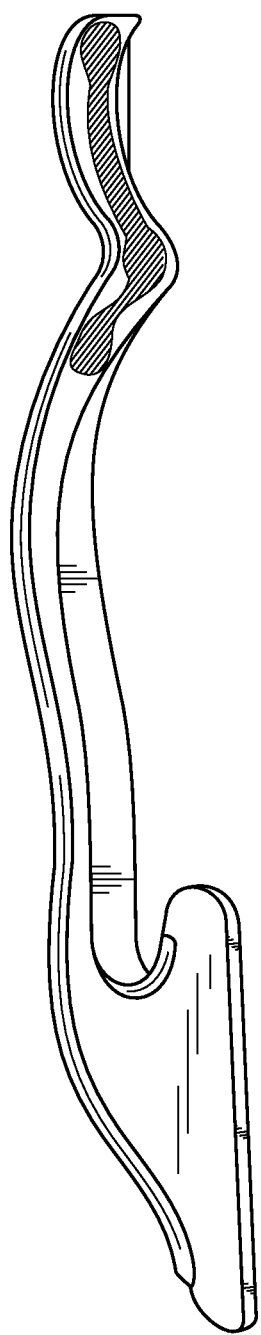
Figure 8:
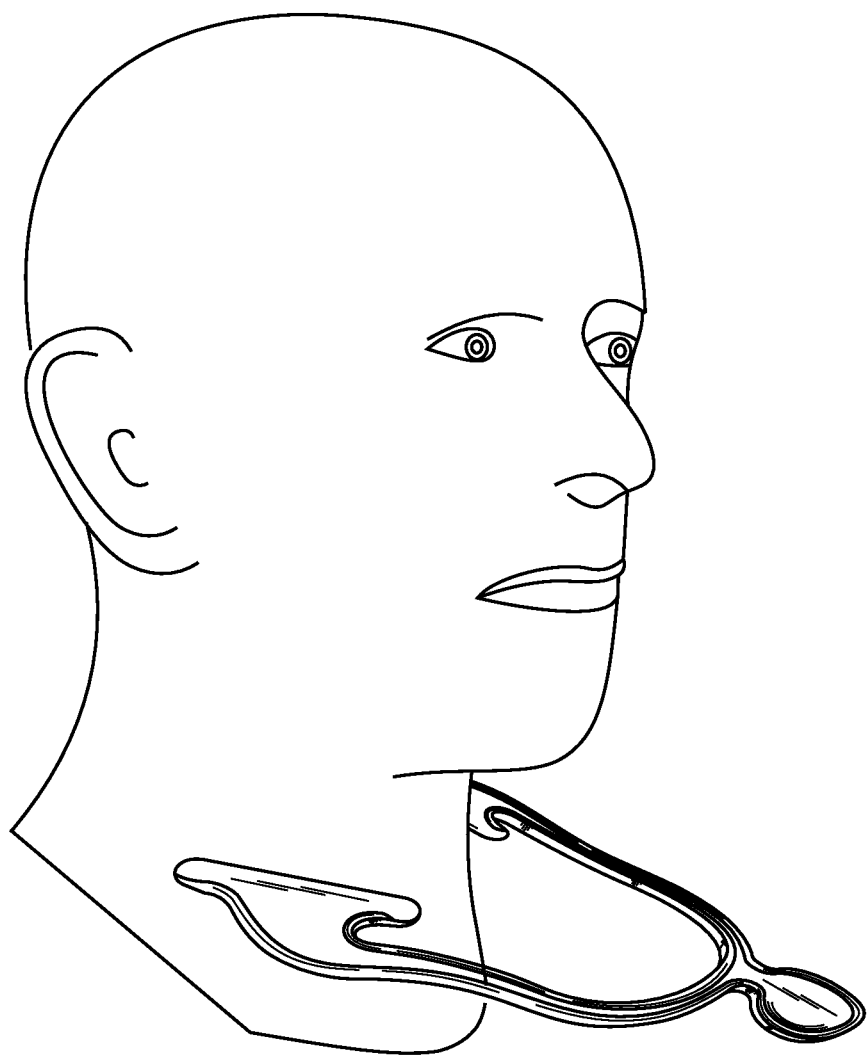
FIGS. 8 and 9 illustrate the application of the device of the present invention to a patient's neck area.

The present invention 110 as shown in FIG. 1 is effectively an EJ tourniquet which, as shown in FIG. 1, has an offset wishbone-like appearance. The two end portions 112, 114 of the wishbone, located distally of the portion of the tourniquet of handle 128 (see FIG. 2) are sized and shaped such that they engage the patient's neck, as shown in FIGS. 7 and 8 to cause a distention of the EJ vein so that IV access is made simply and effectively.

Figure 2:
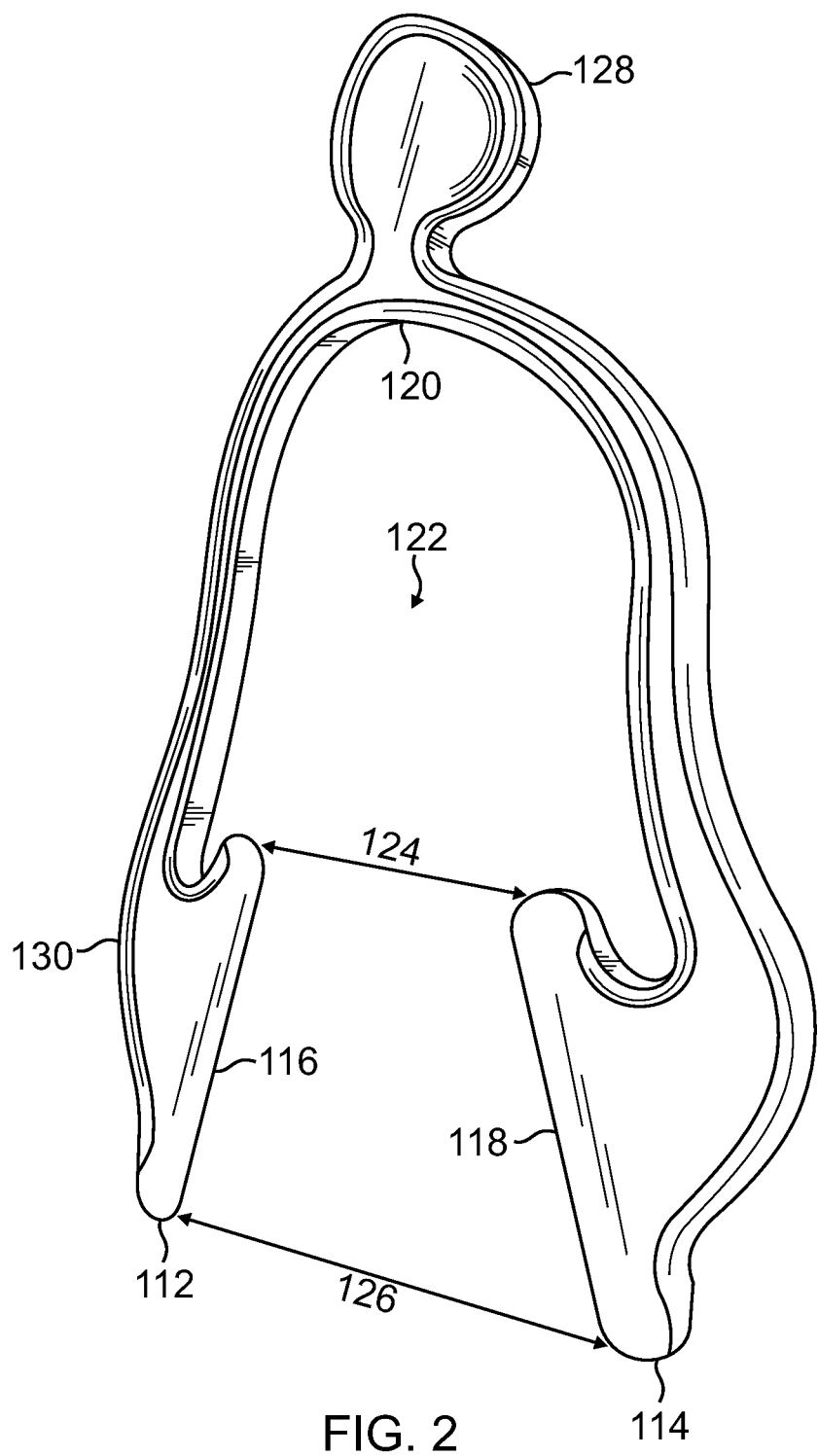
FIG. 2 is another perspective view of the device taken from the opposite of the FIG. 1 perspective.
Figure 3:
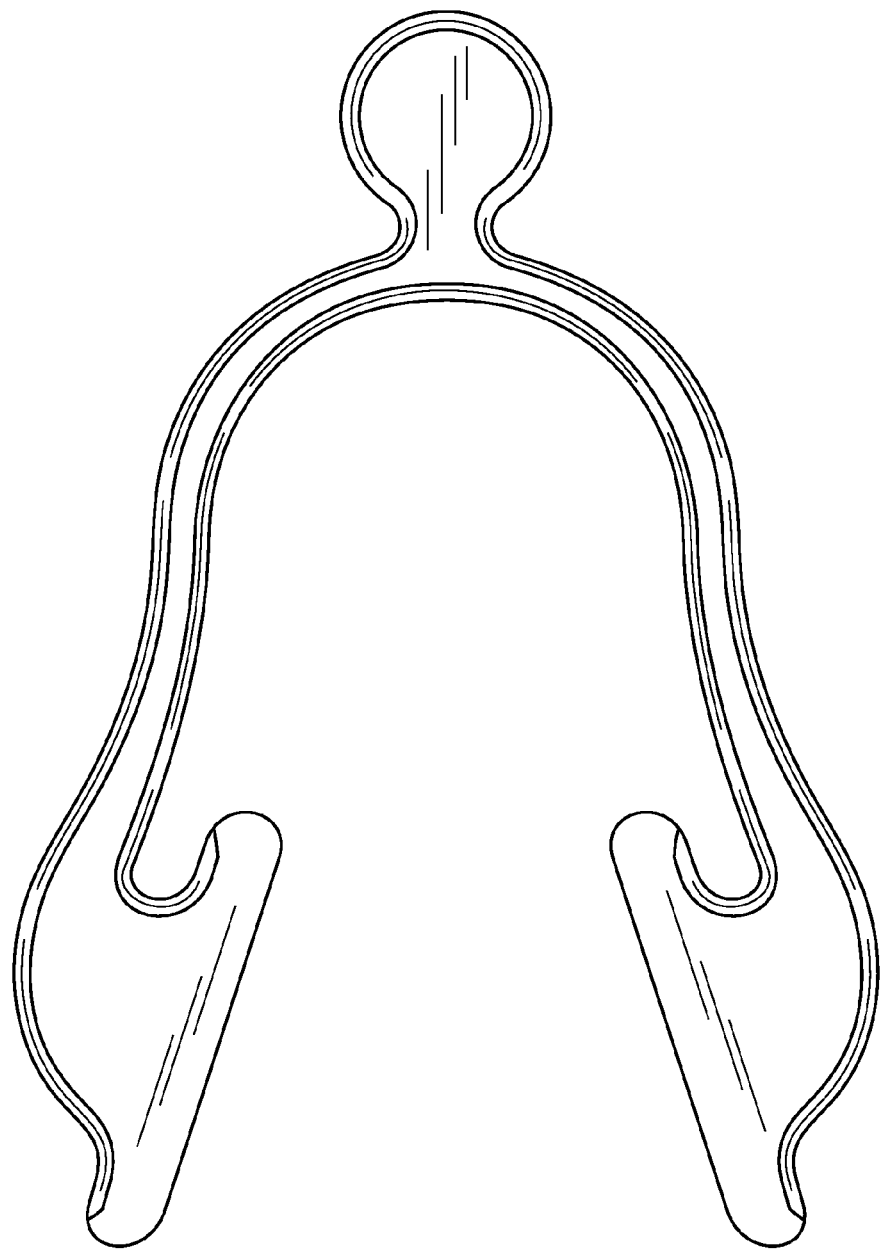
FIG. 3 is a front view of the device of the present invention.

While the shape of the EJ in related applications 61/779, 420 and 29/448,541 is more or less planar, that is, the handle 28 shown in FIG. 2 of such disclosure is more or less coplanar with the two end portions 12, 14 of FIG. 1 of such disclosure, in the present application the respective handle and end portions are not substantially coplanar but rather are offset from one another for handling purposes and to be able to better bring contact to bear on a patient's neck.

As shown in drawing FIGS. 1-6, the EJ tourniquet is a simple device which can be placed on the patient's neck area to cause a bulging of the EJ veins. This is accomplished by having the minimum distance between the ends of the wishbone be less than the width of a patient's neck. Thus, to accommodate different patients' neck sizes and the physiology of the patient, the EJ wishbone may be made in different widths and lengths to accommodate the very differing thicknesses of human anatomy necks. In its simplest form, the EJ tourniquet is comprised of a single piece of resilient material such as plastic, by way of example only, that is placed on the patient's neck area. It is also envisioned that the EJ tourniquet, instead of being made of plastic or other resilient material such as stainless steel, may be made of a material which is sterilizable, and thus allow for multiple uses of the device.

Figure 4:
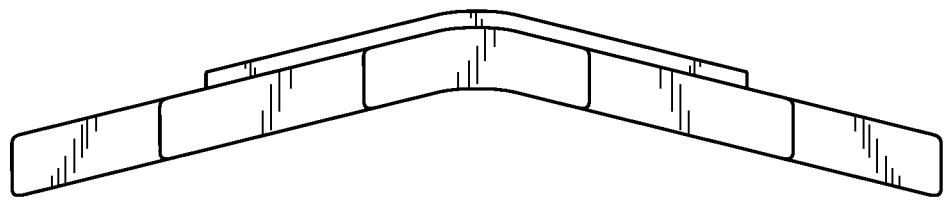
FIGS. 4 and 5 are top and bottom views of the device of the present invention.
Figure 5:
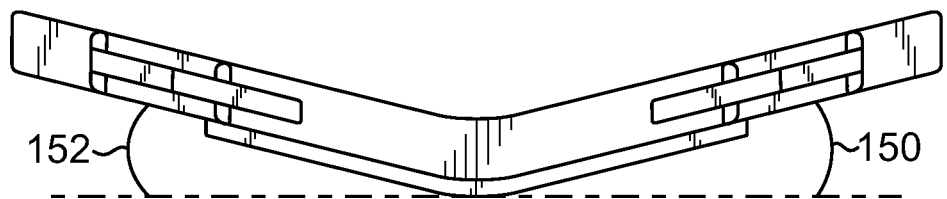
Figure 6:
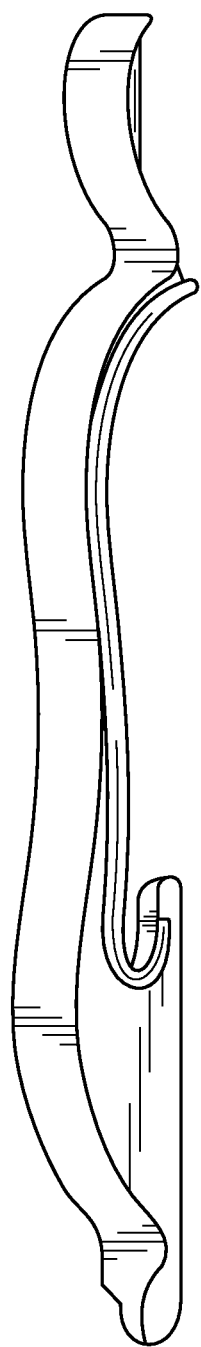
FIGS. 6 and 7 are first and second side views of the device of the present invention.

As can be seen best in FIG. 2, there are two flat surfaces 116 and 118 facing one another and inclined in a manner such that the distance between the flats decreases towards the point of joinder 120. This inclination allows the physician to slide the EJ tourniquet in direction 122 relative to the patient's neck and adjust its position on the patient's neck so that a desired degree of pressure is placed on the patient's neck. Thus, the flat surfaces 116 and 118 engage the EJ in a secure manner and are sufficient width and size to cause distension of the EJ. In addition, the flat inclined surface are not planar with one another, but rather angled with respect to one another, as illustrated in FIGS. 4 and 5. The angular offsets 150 and 152 may range from 12 degrees to 50 degrees. Although the flat surfaces are shown in FIGS. 1 and 2 to be in the shape of linear flat surfaces, it is envisioned that any number of shapes may be incorporated in the end portions of the wishbone so as to adequately engage and distend the EJ vein. As shown in FIG. 2, the distance 126 at the most distal portion of the flat surfaces is greater than the distance less distal from the point of joinder 120. This arrangement has the benefit that a wide range of neck widths may be accommodated, so that at some point along surfaces 116 and 118 the neck of the patient will be engaged sufficiently so as to cause the EJ to become prominent. In particular, it has been found that the distances 124 and 126 (as shown in FIG. 2) between the flat surfaces on either side of the wishbone may range from about 50 mm to about 82.5 mm, as it is desirable to have a separation that provides sufficient pressure on the patient's neck without in fact causing a lessening of or complete cut off of flow of blood. However, any suitable distance range may be used, so long as such distance range is sufficient to adequately engage a patient's neck. In fact, just as persons have widely varying neck sizes, different size EJ tourniquets may also be envisioned. In addition, wherein the EJ tourniquet illustrated and described in Application No. 61/779,420 is shown as substantially planar, in the embodiment of FIG. 2 herein the edge portions 130 are raised in a rib-like fashion to impart strength to the structure of the EJ tourniquet.

A handle 128 as shown in FIG. 2 is located at the closed end of the wishbone and enables the physician or other operator to position the EJ tourniquet onto a patient's neck. While shown in FIG. 2 as being circular with a depression, it is understood that a handle or grab of any size may be incorporated.

Figure 9:
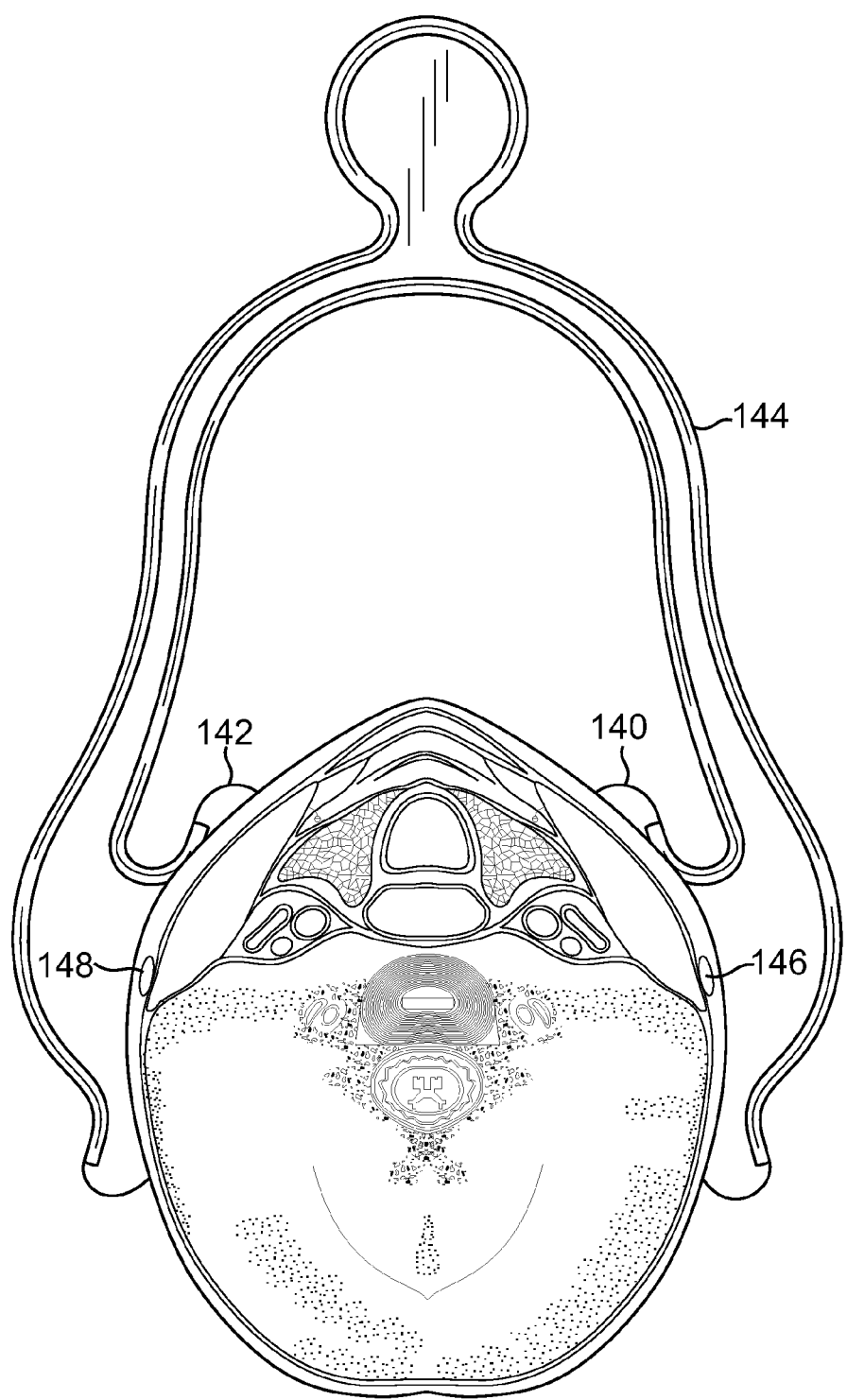

In operation, the patient may be either seated or lying in a flat or almost flat position. It has been found that the seated position is preferably used. This is especially important for elderly patients who may be more comfortable in a sitting position rather than in a flat, reclined position. In the seated position, it has been found that blood tends to collect in the vicinity of the point of contact of the EJ tourniquet with the neck, thus causing an enlarging or distending of the EJ. The doctor or operator then places the EJ tourniquet on the patient's neck in the vicinity of where he or she sees the EJ or determines the EJ should be located if not visible. FIGS. 8 and 9 show the EJ tourniquet as placed onto a patient's neck. In particular, as shown in FIG. 9, the flats 140 and 142 of the device 144 are illustrated as being in place near the EJ veins 146 and 148. Also, as best illustrated in FIG. 8, preferably the EJ tourniquet is oriented such that the EJ tourniquet is in the orientation illustrated in FIG. 8, but this may be varied or reversed in accordance with the wishes of the physician or as dictated by the neck structure of the patient. The correct position of the EJ tourniquet on the patient's neck makes the EJ vein stand out and thus eases the ability to introduce an IV into the patient's vein. Since patients' body physiologies and the location of the EJ vary, the doctor or operator can easily move the EJ tourniquet up, down, towards, and away from the patient's neck until the external jugular vein is located. The EJ Tourniquet may be used in a variety of medical procedures. For example, it may be used in conjunction with ultrasound procedures. If, for example, the physician cannot find a suitable vein in the patient's arm for IV cannulation, the physician can use the EJ tourniquet to cause swelling or distention, apply ultrasound, then cannulate with a needle.

Thus, we have provided an external jugular tourniquet which is simple in structure and in operation, is inexpensive to make, may be disposable, and is sized to occlude the bilateral external jugular vein in a manner that is safe and comfortable for the patient without interrupting breathing or blood flow.

What we claim is:

1. A method of providing access to and distending one or more of the external jugular veins on the neck of a living human patient, the method comprising:

providing a device to engage on both sides of the patient's neck, the device comprising: a wishbone shaped frame, the frame forming a closed end and an open end; the open end having two legs, each leg having a portion connected to the closed end at a common point and each leg having an end surface having a portion located distally of the common point of the closed end, each end surface on the open end of each of the legs being constructed and arranged to face the other end surface on the other leg; and wherein the device is constructed from a substantially resilient material to allow the end surfaces to resiliently press against the one or more jugular veins on both sides of the patient's neck when the device is placed on the patient's neck;

approaching the neck of the patient with the device by moving the open end surfaces on the open end of the device towards and into engagement with both sides of the patient's neck, the end surfaces engaging the patient's neck and the one or more external jugular veins in a non-parallel direction to the orientation of the one or more external jugular veins;

engaging the neck of the patient on both sides of the patient's neck with the end surfaces of the open end of the device until the external jugular vein becomes distended; and, accessing the one or more external jugular veins thus distended.

2. The device of claim 1 wherein the closed end and the open ends are non-coplanar and angularly offset.

3. The device of claim 2 wherein the angular offset ranges from about 12 degrees to about 50 degrees.

4. The device of claim 1 wherein the end surfaces comprise generally flat surfaces, the generally flat surfaces facing each other.

5. The device of claim 4 wherein each flat surface has an end portion and wherein the distance between the end portions most distal from the closed end is greater than the distance between the end portion less distal from the closed end.

6. The device of claim 5 wherein the distances range from about 50 mm to about 82.5 mm.

7. The device of claim 1, further comprising a handle operatively associated with the closed end.

\* \* \* \* \*